(12) United States Patent
Zhou et al.

(10) Patent No.: US 8,329,426 B2
(45) Date of Patent: Dec. 11, 2012

(54) HIGH THROUGHPUT METHOD FOR MEASURING TOTAL FERMENTABLES IN SMALL AMOUNT OF PLANT PART

(75) Inventors: Lan Zhou, Ankeny, IA (US); Xiaoming Bao, Johnston, IA (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 362 days.

(21) Appl. No.: 12/552,574

(22) Filed: Sep. 2, 2009

(65) Prior Publication Data

US 2010/0081582 A1   Apr. 1, 2010

Related U.S. Application Data

(60) Provisional application No. 61/101,869, filed on Oct. 1, 2008.

(51) Int. Cl.
*C12Q 1/20* (2006.01)
*C12Q 1/54* (2006.01)
*C12P 7/06* (2006.01)

(52) U.S. Cl. .............. 435/22; 435/14; 435/161
(58) Field of Classification Search .......... None
See application file for complete search history.

(56) References Cited

U.S. PATENT DOCUMENTS

| | | | | |
|---|---|---|---|---|
| 4,054,671 A * | 10/1977 | Eslick et al. | ................ | 426/16 |
| 4,798,798 A * | 1/1989 | Mehnert et al. | ............ | 435/288.6 |
| 7,309,602 B2 | 12/2007 | David | | |
| 7,968,320 B2 * | 6/2011 | Degre et al. | ................ | 435/161 |
| 2007/0031952 A1 * | 2/2007 | Olsen et al. | ................ | 435/161 |

FOREIGN PATENT DOCUMENTS

| WO | 03/078653 A1 | 9/2003 |
|---|---|---|
| WO | 2007/103786 A2 | 9/2007 |

OTHER PUBLICATIONS

Dien, B., et al., "Fate of Bt Protein and Influence of Corn Hybrid on Ethanol Production," *Cereal Chemistry*, 2002, vol. 79(4), pp. 582-585.

* cited by examiner

*Primary Examiner* — David Naff
(74) *Attorney, Agent, or Firm* — Alston & Bird LLP

(57) ABSTRACT

According to the invention, there is provided a high throughput method for measuring total fermentables using a small amount of plant tissue. A high throughput screening tool for gene discovery aiming for increasing total fermentables is further provided.

13 Claims, 2 Drawing Sheets

HIGH THROUGHPUT METHOD FOR MEASURING TOTAL FERMENTABLES IN SMALL AMOUNT OF PLANT PART

CROSS-REFERENCE TO RELATED APPLICATIONS

This application claims priority under 35 U.S.C. §119 of a provisional application Ser. No. 61/101,869 filed Oct. 1, 2008, and which application is hereby incorporated by reference in its entirety.

FIELD OF INVENTION

This invention relates generally to methods of determining the amount of total fermentables in plant tissue.

BACKGROUND OF INVENTION

Fermentation processes are an important component of many industries. For example, fermentation processes are employed to produce a number of different foods and beverages. Further, the ethanol fuel industry is growing at a rapid pace.

Fermentation processes comprise the fermentation by microbial organisms of fermentable compounds into fermentation products, such as ethanol and carbon dioxide. It is therefore desirable to be able to determine the amount of total fermentable compounds.

The methods currently used for measuring total fermentables require a large scale assay which determines the weight loss of a large quantity of plant tissue caused by carbon dioxide evolution during the fermentation. Such a large scale assay requires a large amount of tissue and has a low throughput. It accordingly would be advantageous to be able to use a high throughput assay for measuring total fermentables in a small amount of plant tissue.

SUMMARY OF INVENTION

According to the present invention, there is provided methods related to a high-throughput method for measuring total fermentable compounds of a plant part having at least one fermentable compound. The at least one fermentable compound is incubated under conditions that allow fermentation of the at least one fermentable compound and which results in a fermentation mixture having ethanol. The fermentation mixture is heated under conditions which allow evaporation of the ethanol and thereby allowing the amount of the at least one fermentable compound to be determined due to the weight loss of the plant part caused by the ethanol evaporation. In an embodiment of the invention, the weight of the plant part is less than 250 milligrams. In a further embodiment, the weight of the plant part is less than 150 milligrams.

Further according to the present invention, there is provided a high-throughput method for measuring total fermentable compounds in a plant tissue. The plant tissue is treated under conditions such that the alpha-amylase present in the plant tissue is allowed to digest the starch present in the plant tissue to form at least one fermentable compound. The at least one fermentable compound is incubated under conditions that allow fermentation of the at least one fermentable compound, wherein the fermentation results in a fermentation mixture having ethanol and carbon dioxide. The fermentation mixture is heated under conditions which allow evaporation of the ethanol. By determining the weight loss of the plant part due to the loss of carbon dioxide during fermentation and to the evaporation of the ethanol the amount of the at least one fermentable compound may be determined.

The present invention further provides a high-throughput screening method for a genetic trait of increased total fermentables. A population of plant tissues is analyzed and the amount of total fermentables is determined using the methods of the present invention. The presence of an increased amount of the at least one fermentable compound in a first plant tissue compared to a second plant tissue is associated with one or more characteristics indicative of a genetic trait associated with increased total fermentables. In an embodiment of the invention, one or more plant tissues is selected from a population of plant tissues based on the presence of one or more characteristics that are associated with one or more transgenes.

DETAILED DESCRIPTION OF INVENTION

Figure 1:
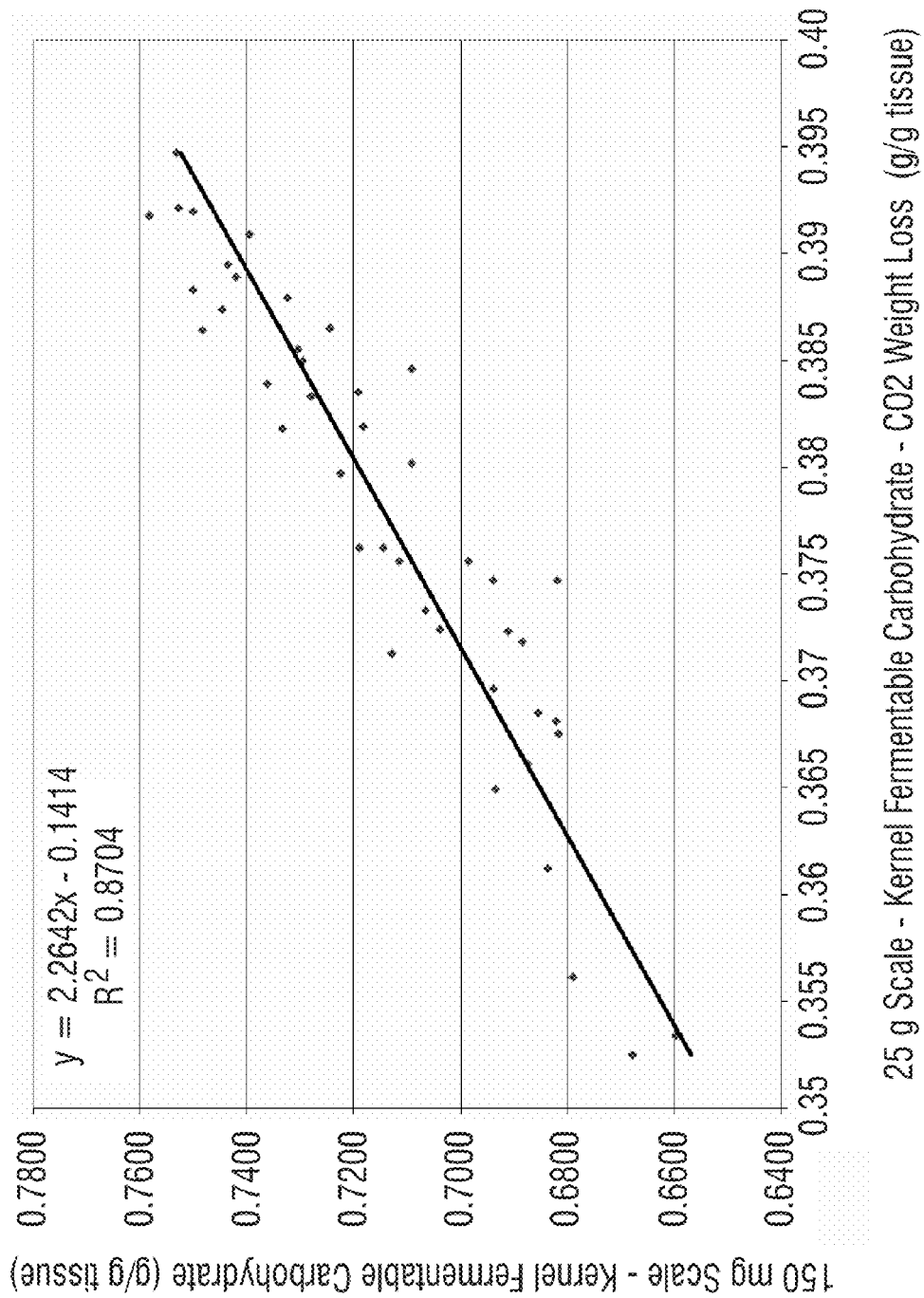
FIG. 1 is a graph illustrating the relationship between total fermentable carbohydrates as measured through traditional, large scale fermentation assays and the claimed assay.

The following description is merely exemplary in nature and is not intended to limit the present disclosure, application, or uses.

A fermentable compound according to the present invention is any compound capable of being fermented. The term "total fermentables" means all or nearly all of the detectable fermentable compounds, for example at least 80%, 85%, 90%, 95%, 98%, 99%, or 100% of the total fermentables.

The term "fermentation product" as used herein means any substance directly resulting from a fermentation reaction according to the present invention. Fermentation products include alcohol and a gaseous product produced by the anaerobic fermentation of the total fermentables. The fermentation product may contain suitable constituent(s) from a fermentation broth. For example, the fermentation residuals may include dissolved and/or suspended constituents from a fermentation broth. The suspended constituents may include undissolved soluble constituents, such as where the solution is supersaturated with one or more components, and/or insoluble materials present in the fermentation broth. The fermentation products may include substantially all of the dry solids present at the end of a fermentation, such as by spray drying a fermentation broth and the biomass produced by the fermentation, or may include a portion thereof. The fermentation products may include crude fermentation product from fermentation.

Fermentation as used herein refers to the oxidation of organic compounds, such as carbohydrates, for energy derivation. Oxidation is performed using an endogenous electron acceptor. The organic compounds usually broken down by fermentation process are sugars. Fermentation as used herein can be anaerobic (deficient in oxygen) as well as aerobic (meaning oxygenated). Under aerobic conditions, microorganisms such as yeast cells can break down sugars to end products such as $CO_2$ and $H_2O$. Under anaerobic conditions, yeast cells utilize an alternative pathway to produce $CO_2$ and ethanol. The fermentation reaction of the present invention is preferably anaerobic, i.e., partially or completely deficient in oxygen and is preferably the conversion of a sugar, particularly glucose or fructose, to alcohol, particularly ethanol, and a gaseous product, particularly carbon dioxide. One molecule of glucose is converted by yeast during the fermentation process into exactly two molecules of ethanol and two molecules of carbon dioxide. This type of fermentation is commonly referred to as ethanol fermentation. Fermentation can also be used to refer to the bulk growth of microorganisms on a growth medium where no distinction is made between aerobic and anaerobic metabolism.

Polysaccharides such as cellulose, starch, and pectin can be hydrolyzed by enzymes such as cellulases, amylases, and pectinases. Most anaerobic bacteria undergo hexose metabolism via the Emden-Meyerhof-Pamas pathway (EMP) which produces pyruvate as an intermediate along with NADH. The pyruvate and NADH generated can then be transformed into fermentation metabolic waste products such as lactate, propionate, acetate, and ethanol by other enzymatic activities which may vary with microorganism species. In hydrolysis and acidogenesis, sugars, amino acids, and fatty acids produced by microorganisms by degradation of biopolymers are metabolized to fermentation endo-products such as lactate, propionate, acetate, carbon dioxide, and ethanol by other enzymatic activities which vary with microorganism species.

The present invention comprises a high throughput method for measuring total fermentables using a small amount of plant tissue. According to the methods of the present invention, the amount of at least one first fermentable compound may be determined.

Further according to the methods of the present invention, the amount of total fermentables may be determined.

According to the present invention, the first fermentable compound and any further fermentable compounds which comprise the total fermentable compounds may individually comprise any organic molecule capable of undergoing fermentation, preferably sugar.

Any sugar capable of undergoing fermentation may be used with the present invention. Sugars capable of undergoing fermentation are well known in the art. Sugars which may be used with the present invention include, but are not limited to, glucose, fructose, sucrose saccharose, maltose, or mixtures thereof.

The present methods may be employed to measure total fermentables in any plant tissue. As used herein, the term "plant tissue" includes leaves, stems, roots, root tips, anthers, seed, grain, embryo, pollen, ovules, flowers, cotyledon, hypocotyl, pod, flower, shoot and stalk, cells and the like. Further as used herein, the term "plant part" includes leaf, stem, root, root tip, anther, seed, grain, embryo, pollen, ovule, flower, cotyledon, hypocotyl, pod, flower, shoot, stalk, tissue, cell and the like. As used herein, the term "plant" includes reference to an immature or mature whole plant, including a plant from which seed or grain or anthers have been removed. Seed or embryo that will produce the plant is also considered to be the plant.

The present invention comprises using a using a small amount of tissue to measure total fermentables. As used herein, small amounts of tissue include, but are not limited to, less then or equal to 25 milligrams, less than or equal to 50 milligrams, less than 100 milligrams, less than 150 milligrams, less than 200 milligrams, less than 250 milligrams, less than 500 milligrams, less then 1 grams, less then 5 grams, less than 10 grams, and less than 20 grams. The amount of tissue to be used in the methods of the present invention preferably include the amount of tissue in a single seed, approximately 100 to 200 milligrams.

There are a variety of plants that can be used in the fermentation methods of the present invention. Suitable plants include, but are not limited to, corn, wheat, soybean, milo, oat, barley, rice, rye, sorghum, potato, whey, sugar beets, taro, cassaya, fruits, fruit juices, and sugar cane may all be used with the present invention. The plants and plant tissue used in the fermentation process of the present invention can be natural, chemically modified, or genetically modified. The examples of plants that may be fermented according to the present invention include, but are not limited to, maize, soybean, rapeseed, sunflower, cotton, tobacco, alfalfa, wheat, barley, oats, sorghum, rice, broccoli, cauliflower, Arabidopsis, cabbage, parsnips, melons, carrots, celery, parsley, tomatoes, potatoes, strawberries, peanuts, grapes, grass seed crops, sugar beets, sugar cane, beans, peas, rye, flax, hardwood trees, softwood trees, and forage grasses. Preferable plants are crop plants for example, maize, soybean, cereals and pulses, wheat, milo, oats, amaranth, rice, sorghum, millet, cassaya, barley, pea, tapioca, taro, potatoes, and other root, tuber, or seed crops.

The present invention preferably comprises the use of maize in the fermentation methods of the present invention. Maize is about two-thirds starch, which is converted during a fermentation and distilling process into ethanol and carbon dioxide. The remaining nutrients or fermentation products can result in condensed distillers solubles or distillers grains such as dried distillers grains with solubles (DDGS), which can be used in feed products. Processes for fermenting and distilling maize are known in the art. In general large scale applications, the process involves an initial preparation step of dry milling or grinding of the maize. The processed maize is then subject to hydrolysis and enzymes added to break down the principal starch component in a saccharification step. The following step of fermentation is allowed to proceed upon addition of a microorganism (e.g. yeast) to produce gaseous products such as carbon dioxide.

The present invention describes a high-throughput method for measuring total fermentables using a small amount of tissue. For example, the starch in a single maize seed comprising 100 to 200 milligrams of plant tissue is converted by the addition of saccharifying enzymes such as alpha-amylase and glucoamylase in to fermentable sugars such as glucose or maltose. During the fermentation by microbial organisms, preferably yeast, the total fermentable compounds are converted into alcohol and other gaseous products. The alcohol preferably comprises ethanol and the gaseous products preferably comprise carbon dioxide.

The present invention comprises calculating the weight loss of the plant tissue due to evolution of a gaseous product during fermentation. A gaseous product according to the present invention is any product produced during fermentation which is in the form of a gas. Preferably the gaseous product is carbon dioxide.

The present invention comprises the step of measuring the amount of gaseous product produced during fermentation of the total fermentables. The gaseous product is measured by inoculating yeast with the plant tissue, where the starch in the tissue has been digested into sugar. During the fermentation by yeast, the sugar is converted into a gaseous product, preferably carbon dioxide. The carbon dioxide is allowed to vent from the fermentation flask during the fermentation process.

After fermentation is completed, the weight loss of the fermentation flask is measured using methods known in the art, such as a Sartorius balance. The evolution of carbon dioxide as a gaseous product which escapes from the fermentation flask accounts for the weight loss of the fermentation flask after fermentation is complete. The present invention comprises the step of measuring total fermentables by measuring the weight loss of the plant tissue caused by the evolution of carbon dioxide during fermentation.

After the fermentation process has completed, the fermentation mixture is heated such that the ethanol produced during the fermentation of the plant tissue is allowed to evaporate. The weight loss of the tissue due to the evolution of the carbon dioxide during the fermentation process and the evaporation of the ethanol during the heat treatment after the fermentation process is then measured.

Because there is a direction correlation between the amount of total fermentables and the amount of ethanol and carbon dioxide produced during the fermentation process, by measuring the weight loss of the plant tissue after the fermentation and after the heat treatment following the fermentation the amount of total fermentables can be determined. Accordingly, the present invention comprises a method for measuring the amount of the total fermentables in the fermentation process by measuring the weight loss of the plant tissue due to the fermentation and the heat treatment after the fermentation.

The present invention comprises high throughput methods of measuring total fermentables in plant tissue. Preferably, total fermentables are measured by determining the weight loss of the plant tissue due to the carbon dioxide evolution during fermentation and due to the loss of ethanol as a result of the heat treatment of the fermentation mixture after fermentation. The present invention further comprises methods of controlling a fermentation process, wherein a composition comprising a small amount of plant tissue comprising total fermentables is incubated with a microbial organism for a tine of incubation, after which a test sample is acquired from said liquid composition and the amount of total fermentables in said composition is determined.

The methods of the present invention comprise the fermentation of total fermentables by a microbial organism and thereby producing assayable products, preferably carbon dioxide and ethanol. The plant tissue and microbial organism should be incubated under conditions which allow the microbial organism to ferment essentially all of the total fermentables. The time of incubation should be selected according to the plant tissue, the microbial organism and the total fermentables to be determined. The incubation of the plant tissue and the microbial organism may be done by any method known in the art. The conditions which will allow the microbial organism to ferment essentially all of the total fermentables are known in the art.

Microbial organisms capable of performing fermentation are known in the art. The microbial organism to be used with the present methods should be selected according to the nature of the total fermentables which are being determined. The microbial organism should be capable of fermenting the fermentable compound.

Suitable microbial organisms that can be used in the fermentation reaction of the present invention include prokaryotic and eukaryotic cell cultures. Biological systems include fungal, bacterial, and microalgal systems. Where the total fermentables comprise sugar, the microbial organism is preferably capable of fermenting sugar and thereby producing alcohol and a gaseous product. The microbial organism to be used with the present invention is preferably yeast, for example *Saccharomyces cerevisiae*. Some of the examples of yeast that can be used in the fermentation process disclosed herein include, but are not limited to, *Saccharomyces cerevisiae, Saccharomyces carlsbergensis, Kluyveromyces lactis, Saccharomyces lactis, K marxianus*, and *K. fragilis* yeasts.

The microbial organisms used with the present invention may be in a dried form and may be dried by any conventional drying method which allows the microbial organism to resume metabolism and growth once the microbial organism is replaced in an aqueous environment. By way of example only, the microbial organism may be dried by air drying, spray drying, freeze drying, drum drying or dried using a tray drier, ring drier, fluid-bed dryer or vacuum-band dryer.

The amount of microbial organism to be used with the methods of the present invention may depend on the total fermentables, the amount and nature of the plant tissue, and the microbial organism to be used.

The conditions allowing the microbial organism to ferment essentially all of the total fermentables should be selected according to the plant tissue and the nature of the microbial organism. Conditions may include incubation for a predetermined period of time. Furthermore, conditions may include incubation at a specific temperature. For most purposes the temperature is in the range of 10° to 30° C.

In addition conditions may comprise shaking, stirring or the like. Shaking and/or stirring may be done using any conventional means known in the art. The fermentation mixture may be submitted to shaking during the entire incubation period or the shaking may be applied only during certain intervals of the incubation period. By way of example only, the fermentation mixture may be submitted to shaking for one to two minutes, from two to five minutes, from five to ten minutes, from ten to 20 minutes, from 20 to 30 minutes, from 30 to 45 minutes, from 45 to 60 minutes, and for more than 60 minutes. By way of example only, the fermentation mixture may be shaken once, twice, three to five times, five to ten times, or ten to 20 times.

The method of determining the amount of at least one fermentable compound in plant tissue of the present invention further comprises repeating the step of determining the amount of total fermentables or at least one fermentable compound as often as desired.

The methods of the present invention may be performed regularly at timely intervals during a fermentation process to determine the amount of fermentable compound present in the plant tissue. The present invention includes, but is not limited to, withdrawing at timely intervals during a fermentation process the samples and performing the methods of the present invention on said samples. The methods may be performed once, twice, three to five times, five to ten times, ten to 20 times, 20 to 30 times, 30 to 50 times, 50 to 100 times, and/or more than a 100 times. The samples may be withdrawn at regular time intervals or they may be withdrawn with varying time intervals.

The methods of the present invention may comprise adding one or more antibiotics to the fermentation mixture. In embodiments of the invention where the microbial organism is yeast, the compositions may comprise one or more antibiotics. The fermentation mixture according to the invention may be placed under conditions wherein microbial growth is possible or promoted, and it may therefore be advantageous to inhibit bacterial growth. By way of example only, the composition may be resuspended in an aqueous medium. In order to prolong the stability of a composition comprising yeast in an aqueous environment bacterial growth is inhibited.

Any antibiotic known in the art may be used with the present invention, including, by way of example only, penicillin, bacitracin, chloramphenicol or valinomycin. The antibiotic should be added to the fermentation mixture in amounts sufficient to inhibit bacterial growth.

The high throughput methods of the present invention describe methods for determining the amount of total fermentables in a small amount of plant tissue. Because of the small amount of tissue used, the methods of the present invention further comprise a high throughput screening tool for the discovery of genes related to increasing total fermentables.

The high throughput screening tool could be used to screen a mapping population or a mutagenized population and sort transgenic events.

As used herein, the term "allele" refers to any of one or more alternative forms of a genetic sequence. In a diploid cell or organism, the two alleles of a given sequence typically occupy corresponding loci on a pair of homologous chromosomes. The term "haploid" refers to a cell or organism having one set of the two sets of chromosomes in a diploid. The term "locus" refers to a defined segment of DNA.

Examples of characteristics indicative of genetic traits include, but are not limited to, genetic markers, restriction fragment length polymorphisms (RFLPs), alleles of genetic markers, genes, quantitative trait loci (QTLs), satellite markers, randomly amplified polymorphic DNAs (RAPDs), arbitrarily primed polymerase chain reaction (AP-PCR), DNA amplification fingerprinting (DAF), sequence characterized amplified regions
(SCARs), amplified fragment length polymorphisms (AFLPs), simple sequence repeats (SSRs) which are also referred to as microsatellites, haplotypes, single nucleotide polymorphisms (SNPs), tag SNPs, DNA-derived sequences, RNA-derived sequences, promoters, 5' untranslated regions of a gene, 3' untranslated regions of a gene, microRNAs, siRNAs, transgene, mRNA, ds mRNA, a transcriptional profile, and a methylation pattern.

Particular markers used for these purposes are not limited to any particular set of markers, but are envisioned to include any type of marker and marker profile which comprises a means of screening a mapping population or a mutagenized population.

Means of performing genetic marker profiles using SSR polymorphisms are well known in the art. SSRs are genetic markers based on polymorphisms in repeated nucleotide sequences, such as microsatellites. A marker system based on SSRs can be highly informative in linkage analysis relative to other marker systems in that multiple alleles may be present. Another advantage of this type of marker is that, through use of flanking primers, detection of SSRs can be achieved, for example, by the polymerase chain reaction (PCR), thereby eliminating the need for labor-intensive Southern hybridization.

The PCR detection is done by use of two oligonucleotide primers flanking the polymorphic segment of repetitive DNA. Repeated cycles of heat denaturation of the DNA followed by annealing of the primers to their complementary sequences at low temperatures, and extension of the annealed primers with DNA polymerase, comprise the major part of the methodology.

Following amplification, markers can be scored by electrophoresis of the amplification products. Scoring of marker genotype is based on the size of the amplified fragment, which may be measured by the number of base pairs of the fragment. While variation in the primer used or in laboratory procedures can affect the reported fragment size, relative values should remain constant regardless of the specific primer or laboratory used.

DNA may be extracted from the sample using any DNA extraction methods known to those of skill in the art which will provide sufficient DNA yield, DNA quality, PCR response, and sequencing methods response. A non-limiting example of suitable DNA-extraction is SDS-based extraction with centrifugation. In addition, the extracted DNA may be amplified after extraction using any amplification method known to those skilled in the art.

Further, RNA may be extracted from the sample using any RNA extraction methods known to those of skill in the art which will provide sufficient RNA yield, RNA quality, PCR response, and sequencing methods response. A non-limiting example of suitable RNA-extraction methods is SDS-based extraction with centrifugation with consideration for RNase-free reagents and supplies. In addition, the extracted RNA may be amplified after extraction using any amplification method known to those skilled in the art.

The extracted nucleic acids are analyzed for the presence or absence of a suitable genetic polymorphism. A wide variety of genetic markers for the analysis of genetic polymorphisms are available and known to those of skill in the art. As used herein, genetic markers include, but are not limited to, simple sequence repeats (SSRs), single nucleotide polymorphisms (SNPs), insertions or deletions (Indels), single feature polymorphisms (SFPs) or transcriptional profiles, and nucleic acid sequences. The analysis may be used to select for genes, QTL, alleles, or genomic regions (haplotypes) that comprise or are linked to a genetic marker. Herein, analysis methods are known in the art and include, but are not limited to, PCR-based detection methods (for example, TaqMan assays), microarray methods, and nucleic acid sequencing methods. The genes, alleles, QTL, or haplotypes to be selected for can be identified using newer techniques of molecular biology.

Any seed can be utilized in a method or device of the present invention. In a particular embodiment, the seed is selected from the plant group consisting of maize, soybean, rapeseed, sunflower, cotton, tobacco, alfalfa, wheat, barley, oats, sorghum, rice, broccoli, cauliflower, Arabidopsis, cabbage, parsnips, melons, carrots, celery, parsley, tomatoes, potatoes, strawberries, peanuts, grapes, grass seed crops, sugar beets, sugar cane, beans, peas, rye, flax, hardwood trees, softwood trees, and forage grasses. In a more particular embodiment, the seed is selected from the group consisting of cotton seed, cucumber seed, maize seed, melon seed, soybean seed, rapeseed seed, rice seed and wheat seed. In an even more particular embodiment, the seed is a maize seed.

In another embodiment, crops analyzed by the methods described herein include forage crops, oilseed crops, grain crops, fruit crops, ornamental plants, vegetable crops, fiber crops, spice crops, nut crops, turf crops, sugar crops, beverage crops, tuber crops, root crops, and forest crops.

In one embodiment, the seed is selected based on the presence or absence of one or more characteristics that are genetically linked with a QTL. Alternatively, the seed can be selected based on the presence or absence of one or more characteristics that are genetically linked with a haplotype associated with a QTL.

Selection of a breeding population could be initiated as early as the F2 breeding level, if homozygous inbred parents are used in the initial breeding cross. An F1 generation could also be sampled and advanced if one or more of the parents of the cross are heterozygous for the alleles or markers of interest. The breeder may analyze an F2 population to retrieve the marker genotype of every individual in the population. Initial population sizes, limited only by the number of available seeds for analysis, can be adjusted to meet the desired probability of successfully identifying the desired number of individuals. See Sedcole, J. R. "Number of plants necessary to recover a trait." Crop Sci. 17:667-68 (1977). Accordingly, the probability of finding the desired genotype, the initial population size, and the targeted resulting population size can be modified for various breeding methodologies and inbreeding level of the sampled population.

Molecular markers, which includes markers identified through the use of techniques such as Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs) and Single Nucleotide Polymorphisms (SNPs), may be used to identify genetic compositions.

Isozyme Electrophoresis and RFLPs have been widely used to determine genetic composition. Shoemaker and Olsen, ((1993) Molecular Linkage Map of Soybean (*Glycine max* L. Merr.). p. 6.131-6.138. In S. J. O'Brien (ed.) Genetic Maps: Locus Maps of Complex Genomes. Cold Spring Harbor Laboratory Press. Cold Spring Harbor, N.Y.), developed a molecular genetic linkage map that consisted of 25 linkage groups with about 365 RFLP, 11 RAPD (random amplified polymorphic DNA), three classical markers, and four isozyme loci. See also, Shoemaker R. C. 1994 RFLP Map of Soybean. P. 299-309 in R. L. Phillips and I. K. Vasil (ed.), DNA-based markers in plants. Kluwer Academic Press Dordrecht, the Netherlands.

SSR technology is currently the most efficient and practical marker technology; more marker loci can be routinely used and more alleles per marker locus can be found using SSRs in comparison to RFLPs. Single Nucleotide Polymorphisms may also be used to identify the unique genetic composition and progeny varieties retaining that unique genetic composition. Various molecular marker techniques may be used in combination to enhance overall resolution.

One use of molecular markers is Quantitative Trait Loci (QTL) mapping. QTL mapping is the use of markers, which are known to be closely linked to alleles that have measurable effects on a quantitative trait. Selection is based upon the accumulation of markers linked to the positive effecting alleles and/or the elimination of the markers linked to the negative effecting alleles from the plant's genome.

Molecular markers can also be used for the selection of qualitative traits. For example, markers closely linked to alleles or markers containing sequences within the actual alleles of interest can be used to select plants that contain the alleles of interest. The use of molecular markers in the selection process is often called genetic marker enhanced selection.

Mass selection is a useful technique when used in conjunction with molecular marker enhanced selection. In mass selection seeds from individuals are selected based on phenotype or genotype. These selected seeds are then bulked and used to grow the next generation. Bulk selection requires growing a population of plants in a bulk plot, allowing the plants to self-pollinate, harvesting the seed in bulk and then using a sample of the seed harvested in bulk to plant the next generation. Also, instead of self pollination, directed pollination could be used as part of the breeding program.

The selected seeds may be bulked or kept separate depending on the breeding methodology and target. For example, when a breeder is analyzing an F2 population for a single gene trait, all individuals with the desired genotype may be bulked and planted in the breeding nursery. Conversely, if multiple QTL with varying effects for a trait are being selected from a given population, the breeder may keep individual identity preserved, going to the field to differentiate individuals with various combinations of the target QTL.

Several methods of preserving single seed identity can be used while transferring seed from the sampling location to the field. Methods include, but are not limited to, transferring selected individuals to seed tape, a cassette tray, or indexing tray, transplanting with peat pots, and hand-planting from individual seed packets. Multiple cycles of selection can be utilized depending on breeding targets and genetic complexity.

The high throughput screening tool of the present invention can also be used to screen a mutagenized population and sort transgenic events. A genetic map can be generated, primarily via conventional Restriction Fragment Length Polymorphisms (RFLP), Polymerase Chain Reaction (PCR) analysis, Simple Sequence Repeats (SSR) and Single Nucleotide Polymorphisms (SNP) that identifies the approximate chromosomal location of the integrated DNA molecule. For exemplary methodologies in this regard, see Glick and Thompson, METHODS IN PLANT MOLECULAR BIOLOGY AND BIOTECHNOLOGY 269-284 (CRC Press, Boca Raton, 1993). Map comparisons involve hybridizations, RFLP, PCR, SSR and sequencing, all of which are conventional techniques. SNPs may also be used alone or in combination with other techniques.

All publications, patents and patent applications mentioned in the specification are indicative of the level of those skilled in the art to which this invention pertains. All such publications, patents and patent applications are incorporated by reference herein for the purpose cited to the same extent as if each was specifically and individually indicated to be incorporated by reference herein.

The claimed invention has been described in detail throughout the specification by way of illustration and example for purposes of clarity and understanding. As is readily apparent to one skilled in the art, the foregoing are only some of the methods and compositions that illustrate the embodiments of the foregoing invention. It will be apparent to those of ordinary skill in the art that variations, changes, modifications and alterations may be applied to the compositions and/or methods described herein without departing from the true spirit, concept and scope of the invention.

EXAMPLES

Example 1

Assay Measuring Fermentable Carbohydrate in a Single Seed

An assay for measuring the fermentable carbohydrate in a single seed of maize was conducted in two steps, the first step being the digestion of starch in a ground kernel using alpha-amylase and Glucoamylase and the second step being the fermentation of the resulting glucose into to ethanol and carbon dioxide by yeast.

A 12.7×3 mm stir bar was placed into a 2 ml snap cap tube (VWR Cat #20170-170), the weight of the tube with the stir bar was recorded. Four other 2 ml tubes were also prepared to serve as reagent control tubes. A single seed was ground using a Genogrinder and 100-200 mg of ground tissue were placed into the pre-weighed tube, the reagent tubes did not receive any ground tissue. 451 µl of alpha-amylase solution was added to each tube where the solution was comprised of approximately 18% to 31% solids. Tube locks (VWR Cat #14229-940) were then placed on the tubes, which were then placed in a boiling water bath for 15 minutes with the solution inside the tubes being stirred throughout the bath. After the bath the tube locks were removed and the tubes were spun down for a short amount of time. After the tubes had cooled, the pH of the solution was adjusted to 4.5 by the addition of 8 µl of 1M HCL to each tube. 6 µl of 5×diluted Glucoamylase (G-ZYME G990 SP, Enzyme Development Corp.) was added to each tube and the tubes were then incubated on a stirring plate at 50° C. for 1.5 hours while stirring. The tubes were then removed, spun down, and cooled to room temperature.

In the fermentation step, approximately 3 mg of yeast was added to the tube containing ground tissue and the tube was then weighed and recorded. Care was taken to avoid yeast adhering to the cap and sides of the tube. The tubes were then spun down, a hole was made in the cap using a needle, and the contents were mixed by stirring. The tubes were then placed in a 30° C. incubator for 48 hours and were stirred at 18 and 24 hours of incubation. After incubation, the tubes were placed on an 80° C.-85° C. heat block for 24 hours. The tubes were then weighed.

Based on the measurements taken during the assay, the total fermentable carbohydrates per tissue (g/g) can be calculated using the following formula:

$$TFCT=(B*0.9-((D-A)*1000-(C*0.95)-E))/(B*0.9)$$

Where:
TFCT: Total fermentable carbohydrates per tissue (g/g)
A: weight of tube+stir bar (g)
B: weight of tissue (mg). Moisture measurement is not necessary. 10% moisture is used.
C: weight of yeast (mg). It has 5% moisture (measured).
D: weight of the tube after heat (g)
E: average of weight gain in reagent control tubes after heat (mg). This needs to be measured along with samples every time
Solutions and Other Materials:
2 M Urea stock solution: For 100 ml, dissolve 12.012 g Urea (anhydrous mol wt 60.06) in dH2O and fill to 100 ml with dH2O. Filter sterilize and store at 40 C.
Final concentration in fermentation: 20 mM
200 mM CaCl2 stock solution: For 100 ml, dissolve 2.94 g CaCl2.2H20 (f.w. 147.0) in dH2O and fill to 100 ml with dH2O. Filter sterilize and store at 40C.
Final concentration in fermentation: 2 mM
Alpha-amylase solution: For 13.2 ml, add 180 µl of 200 mM CaCl2, 180 µl of 2 M of Urea, 36 µl of alpha-amylase (G-ZYME G995, Enzyme Development Corp.) and fill to 13.2 ml with dH2O. Add 8 µl of 1 N NaOH to adjust pH to 6.5.

For 100 assays (96 samples+4 reagent controls) add 720 µl of 200 mM CaCl2, 720 µl of 2 M of Urea, 144 µl of alpha-amylase (G-ZYME G995, Enzyme Development Corp.) and fill to 52.8 ml with dH2O. Add 32 µl of 1 N NaOH to adjust pH to 6.5 (Check the pH).

Example 2

Comparison with Traditional Large Scale Fermentation Assays

The results obtained by the aforementioned technique compare favorably with those obtained by a pre-existing large scale fermentation assay (the 25 g Conventional HTF assay by Cindi Zimmerman, Cereal Chem 79(4):582-585, 2002). As shown in FIG. 1 the results produced by the assay show high correlation with the pre-existing techniques. The aforementioned technique also measures weight lost to both fermentation ($CO_2$) and heat (ethanol) hence it considers the totality of the products of fermentation.

Example 3

Total Fermentable Carbohydrates per Tissue as an Estimate of Kernel Starch

Figure 2:
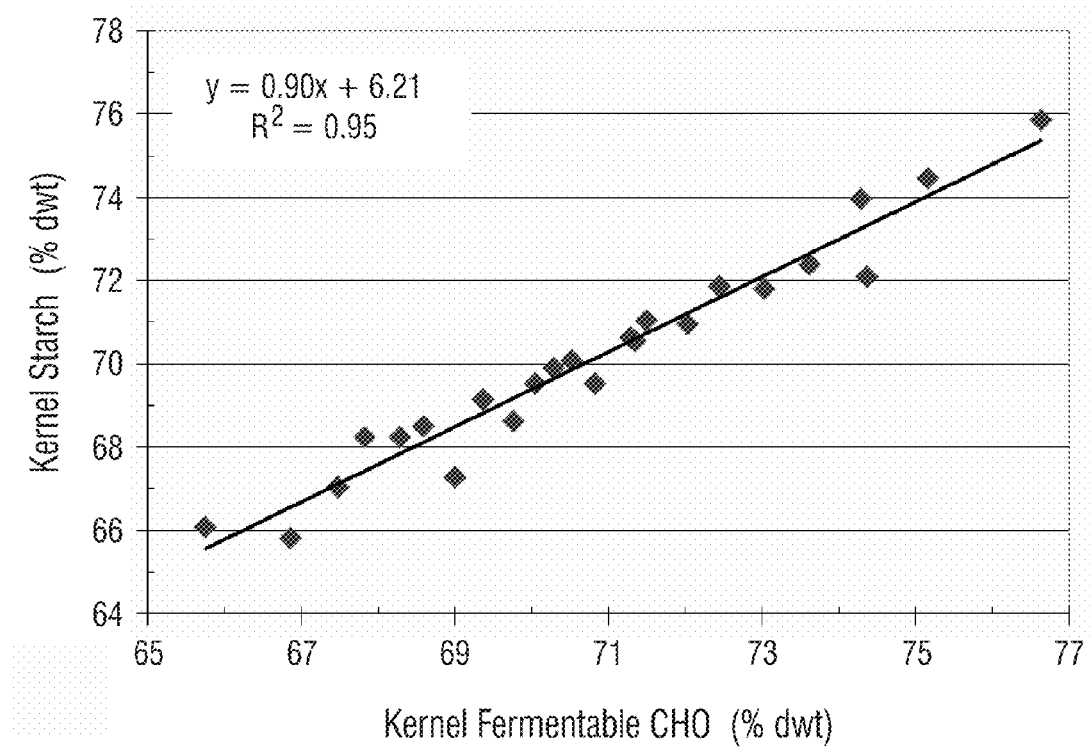
FIG. 2 is a graph illustrating the relationship between total fermentable carbohydrates measured by the claimed assay and kernel starch as measured using traditional methods.

FIG. 2 demonstrates that the total fermentable carbohydrate per tissue is also highly correlated with the kernel starch. As such, total fermentable carbohydrate per tissue may also serve as a substitute estimate for kernel starch, a measurement which is labor intensive and time consuming. The present method can give an estimate of kernel starch with higher throughput and better precision.

What is claimed is:

1. A high-throughput method for measuring total fermentable compounds in a plant part, the method comprising:
providing less than 250 milligrams of the plant part, wherein the plant part is selected from a leaf, stem, root, root tip, anther, seed, grain, embryo, pollen, ovule, flower, cotyledon, hypocotyl, pod, flower, shoot and stalk, and wherein the plant part comprises at least one fermentable compound;
incubating the at least one fermentable compound under conditions that allow fermentation of the at least one fermentable compound, wherein the fermentation results in a fermentation mixture comprising ethanol;
heating the fermentation mixture under conditions that allow evaporation of the ethanol; and
determining the weight loss of the plant part due to heating the fermentation mixture under conditions that allow evaporation of the ethanol and thereby determining the amount of said at least one fermentable compound in the plant part.

2. The method of claim 1 wherein the weight of the plant part comprising at least one fermentable compound is less than 150 milligrams.

3. The method of claim 1 wherein the plant part is obtained from the group consisting of maize, soybean, rapeseed, sunflower, cotton, tobacco, alfalfa, wheat, barley, oats, sorghum, rice, broccoli, cauliflower, Arabidopsis, cabbage, parsnips, melons, carrots, celery, parsley, tomatoes, potatoes, strawberries, peanuts, grapes, grass seed crops, sugar beets, sugar cane, beans, peas, rye, flax, hardwood trees, softwood trees, and forage grasses.

4. The method of claim 1 wherein the at least one fermentable compound comprises monosaccharides, oligosaccharides, or polysaccharides.

5. The method of claim 1 wherein the at least one fermentable compound comprises glucose, fructose, sucrose, saccharose, maltose, or mixtures thereof.

6. The method of claim 1 wherein the fermentation mixture comprises carbon dioxide and ethanol.

7. The method of claim 6 further comprising the step of determining the weight loss of the plant part due to loss of carbon dioxide during fermentation of the at least one fermentable compound.

8. A high-throughput method for measuring total fermentable compounds in a plant tissue, the method comprising:
treating less than 250 milligrams of the plant tissue, wherein the plant tissue is selected from a leaf, stem, root, root tip, anther, seed, grain, embryo, pollen, ovule, flower, cotyledon, hypocotyl, pod, flower, shoot and stalk, and wherein the plant tissue comprises an alpha-amylase and starch, under conditions that allow the alpha-amylase to digest the starch to form at least one fermentable compound;
incubating the at least one fermentable compound under conditions that allow fermentation of the at least one fermentable compound, wherein the fermentation results in a fermentation mixture comprising ethanol and carbon dioxide;
heating the fermentation mixture under conditions that allow evaporation of the ethanol; and
determining the weight loss of the plant part due to loss of carbon dioxide during fermentation of the at least one fermentable compound and to heating the fermentation mixture under conditions that allow evaporation of the ethanol and thereby determining the amount of said at least one fermentable compound.

9. The method of claim 8 wherein the weight of the plant part comprising at least one fermentable compound is less than 150 milligrams.

10. The method of claim 8 wherein the plant tissue further comprises at least one enzyme selected from the group consisting of glucoamylase, alpha-glucosidase, glucose isomerase, and pullulanase.

11. The method of claim 8 wherein the plant tissue is obtained from the group consisting of maize, soybean, rapeseed, sunflower, cotton, tobacco, alfalfa, wheat, barley, oats, sorghum, rice, broccoli, cauliflower, Arabidopsis, cabbage, parsnips, melons, carrots, celery, parsley, tomatoes, potatoes, strawberries, peanuts, grapes, grass seed crops, sugar beets, sugar cane, beans, peas, rye, flax, hardwood trees, softwood trees, and forage grasses.

12. The method of claim 8 wherein the at least one fermentable compound comprises monosaccharides, oligosaccharides, or polysaccharides.

13. The method of claim 8 wherein the fermentable compound comprises glucose, fructose, saccharose, maltose, or mixtures thereof.

* * * * *